United States Patent [19]

Hirshowitz et al.

[11] Patent Number: 5,263,971
[45] Date of Patent: Nov. 23, 1993

[54] APPARATUS FOR THE CLOSURE OF WIDE SKIN DEFECTS BY STRETCHING OF SKIN

[75] Inventors: Bernard Hirshowitz; Amnon Levy, both of Haifa, Israel

[73] Assignee: Life Medical Sciences, Inc., Princeton, N.J.

[21] Appl. No.: 835,636

[22] Filed: Feb. 13, 1992

[30] Foreign Application Priority Data

Feb. 13, 1991 [IL] Israel ............................... 97225

[51] Int. Cl.⁵ .............................................. A61B 17/00
[52] U.S. Cl. .................................. 606/216; 606/213; 606/218; 606/148; 606/1
[58] Field of Search ............... 606/218, 217, 216, 215, 606/213, 150, 148, 151, 212

[56] References Cited

U.S. PATENT DOCUMENTS

| | | | |
|---|---|---|---|
| 268,632 | 12/1882 | Danforth | 606/221 X |
| 583,455 | 6/1897 | Bush | 606/212 |
| 4,512,346 | 4/1985 | Lemole | 606/216 |
| 4,896,680 | 1/1990 | Hirshowitz | |
| 5,009,663 | 4/1991 | Broomé | 606/215 X |

FOREIGN PATENT DOCUMENTS

| | | | |
|---|---|---|---|
| 3227984 | 2/1984 | Fed. Rep. of Germany | |
| 1412751 | 7/1988 | U.S.S.R. | 606/216 |
| 1556666 | 4/1990 | U.S.S.R. | 606/218 |
| 1560132 | 4/1990 | U.S.S.R. | 606/148 |
| 1560133 | 4/1990 | U.S.S.R. | 606/148 |

OTHER PUBLICATIONS

Cohen and Cosmetto, "Suture Tension Adjustment Reel", *J. Dermatol. Surg. Oncol.*, 1992; 18:112-123.

Primary Examiner—Stephen C. Pellegrino
Assistant Examiner—Jeffrey A. Schmidt
Attorney, Agent, or Firm—Robert J. Koch

[57] ABSTRACT

An apparatus for closing wide skin defects may include two long pins for insertion underneath the skin close to the margins of the defect. Two U-shaped members may also be provided. Each U-shaped member may include a sharp hook at the end of each leg adapted to pierce the skin and to engage one pin each in two places. A contracting screw may connect the two members and approximate the pins and the skin margins until final closure of the defect. A parallel alignment mechanism may also be provided to maintain the U-shaped members in parallel alignment.

14 Claims, 3 Drawing Sheets

APPARATUS FOR THE CLOSURE OF WIDE SKIN DEFECTS BY STRETCHING OF SKIN

BACKGROUND OF THE INVENTION

The invention relates to apparatus serving to stretch skin so as to cover an open wound and to enable the surgeon to suture together the opposite skin margins. It relates especially to apparatus to be used during operations following wide excision of skin lesions or for closure of skin defects or otherwise damaged skin areas, thereby obviating the conventional method of using local skin flaps or grafting of skin from other body portions.

U.S. Pat. No. 4,896,680, by one of the present inventors, Bernard Hirshowitz, describes a method and apparatus for stretching the skin over a wound by load cycling including applying a pulling force on opposite skin margins during several periods interrupted by relaxation periods. In this way the skin can be stretched over a wide area in a manner not previously used until the invention by Bernard Hirshowitz. The above patent discloses a surgical stretching apparatus which comprises two pins to be inserted into the skin along both edges of the wound which are gradually pulled together by means of a flexible strap. According to the invention the pulling is done in intervals to allow the collagen fibres of the skin to rearrange themselves for further stretching. The pins of the described apparatus are more or less in the shape of safety pins each provided with a loop for attachment to the flexible strap; the strap, for its part, has projections or apertures for engagement with a ratchet-shaped device which will hold the two pins in forceful apposition.

It has, however been shown that the described apparatus has certain drawbacks which should be overcome by the present invention, the main drawback being that after the two pins have been drawn together, they do not leave room for suturing the approximated skin margins. Another drawback is that manual pulling on the flexible strap is rather crude, in that the pulling force cannot be minutely controlled. And finally that the two pins grip only relatively narrow strips of skin along both edges, thereby not permitting closure of a wide wound by one pulling operation.

It is, therefore, an object of the invention to provide an apparatus which will permit suturing together of the skin edges while the stretching apparatus is in situ without disturbing the suturing operation.

It is another object to permit insertion into the skin edges of longer pins adapted to grip practically the entire length of the wound and to permit shifting of the stretching means along the wound edges thereby enabling the two pins to be engaged in different locations.

And it is a further object to permit prolonged use of the apparatus as well as the pins, contrarywise to the apparatus described in the previous patent which had to be disposed after one use.

SUMMARY OF THE INVENTION

A preferred embodiment of the apparatus for stretching skin comprises essentially; 1. two long pins to be inserted under the skin along the two edges of a wound to be closed; 2. two U-shaped retaining members each having a top surface, and a bottom surface to be placed close to the skin, each member being provided with a sharp hook at the end of each leg of the "U"; 3. contracting means for pulling and approximating the two retaining members with their legs extending towards the open wound. The retaining members are adapted to be placed behind the pins in opposite alignment with their hooks piercing the skin and engaging the respective pin in a position along the wound edges. The contracting means are designed to pull the two retaining members slowly and gradually together so as not to cause damage to the skin area. The U-shape permits suturing of the skin edges with the apparatus in position, due to the open spaces left between and on both sides of the two legs.

A preferred embodiment of the contracting means comprises two contractor arms in parallel alignment, connected by a screw means adapted to approximate the two components by rotating the screw mechanism. One end of each contractor arm is in the shape of a bar of smooth, even cross section adapted to retain one retaining member each in opposite alignment on both sides of a wound and to allow shifting of each retaining member along its respective bar. The contractor arms are preferably slidably connected at their other ends by a smooth bar engaging with bores in corresponding locations with a view to keeping the two arms in parallel alignment. Each U-shaped retaining member includes two legs with outwardly bent hooks at the bottom surface of their ends connected by a longitudinally perforated flange adapted to be slidingly mounted on the smooth bar of a contractor arm.

After the two pins have been inserted along the wound margins, the apparatus is placed across the wound with the retaining members positioned behind the skin margins, while the hooks are pressed through the skin into engagement with the pins. Now the screw mechanism is rotated so as to slowly approximate the two contractor arms and the attached retaining members and the operation is continued at intervals as described in the aforementioned patent.

Another embodiment of the apparatus includes two U-shaped retaining members having forwardly bent hooks attached to the underside of the legs at their respective ends, a connecting flange provided with a lug protruding out of its top surface which is perforated and provided with screw thread for engagement with a screw adapted to be rotated for the purpose of approximating the two members. A preferred embodiment of the apparatus includes one screw-threaded member and one smooth-bored member, and a screw provided with a collar at its one end engaging with the smooth bore and screw thread over its remaining length engaging with the screw-threaded member. The drawback of this apparatus, compared with the afore-described one, lies in the obstruction caused by the screw preventing suturing of the area between the two legs.

Other contracting mechanisms may be provided for approximating the two retaining members, but it will be understood that the essence of the invention lies in the shape of the two retaining members which permits suturing of the wound margins while the apparatus is still in situ, pulling the margins together.

DETAILED DESCRIPTION OF THE PREFERRED EMBODIMENT

Figures 1, 2:
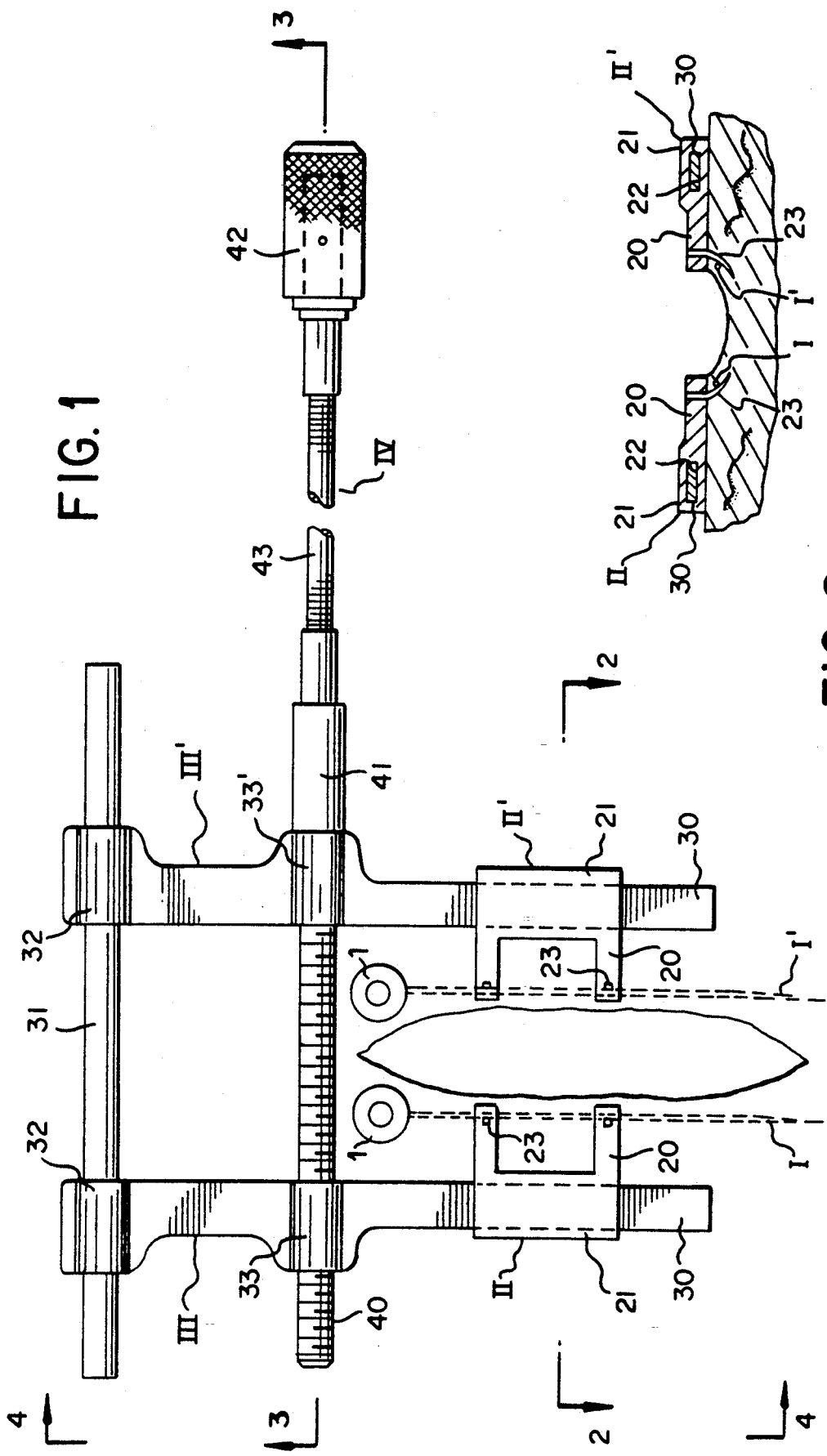
FIG. 1 is a plan view of an apparatus positioned over an open skin wound.
FIG. 2 is a section through the apparatus along line A—A of FIG. 1.
Figure 4:
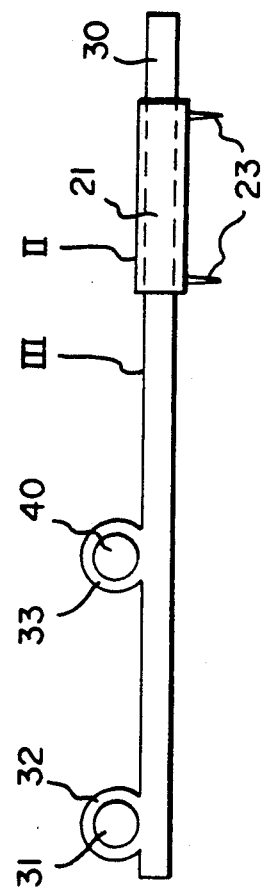
FIG. 4 is a side view of the apparatus along line C—C of FIG. 1.
Figure 3:
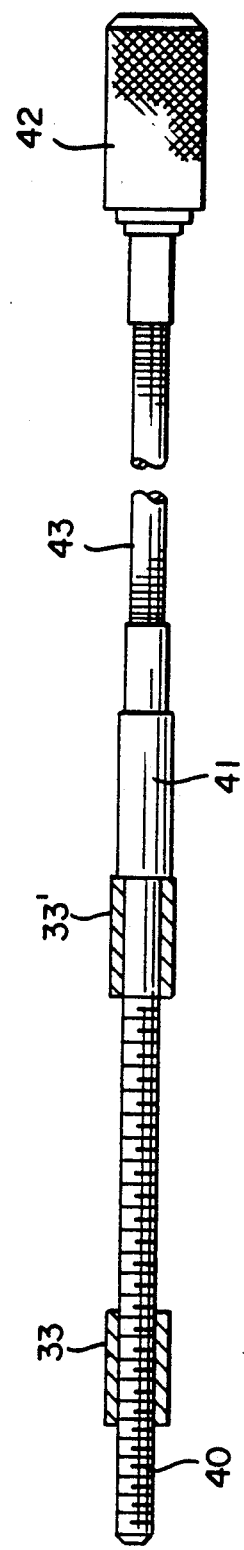
FIG. 3 is a section through the apparatus along line B—B of FIG. 1.

With reference to FIGS. 1 through 4 of the drawings the skin stretching apparatus comprises two long pins I and I' each provided with a head 1 which are inserted under the skin along the wound margins as shown in FIGS. 1 and 2, and two retaining members II and II' each engaging one of the two pins. Each retaining member is in a U-shape and comprises two parallel, spaced-apart legs 20 connected by a flange 21 which is longitudinally perforated by a bore of rectangular cross section (22). Forwardly extending hooks 23 are connected to the underside of the members one each at the end of each leg 20 which are shown to have pierced the skin and to have engaged the pins from the side remote from the wound. The retaining members are held in position by two contractor arms III and III' and are slidingly mounted on the bar-shaped ends 30 by their rectangular bores 22. The contractor arms are held in parallel alignment by a cylindrical bar 31 which extends through horizontal bores in lugs 32 at the other ends of the arms. A screw IV is adapted to pull the two arms together and extends through a screw-threaded bore in a lug 33 on the top surface of the arm III and through a smooth bore in a lug 33' on the top surface of the arm III'. The screw IV includes a screw-threaded end 40, a collar 41 abutting the lug 33' of arm III' and a handle or knob 42 attached to the screw IV by a flexible tube or helical spring 43. BY rotating the handle 42 the screw-threaded end in engagement with the thread in the lug 33 pulls the arms III and III' to each other whereby the retaining members II and II' contract the wound margins by means of the hooks 23 and the pins I and I'. As described in the previous patent, the operation is performed in several stages to allow the skin to stretch in a gradual manner during intervals between the stretching stages. After the wound margins have been contacted the wound is sutured in a manner known to the art, whereby it is evident that the legs 20 do not interfere with the operation, being remote from the margins.

Figure 5:
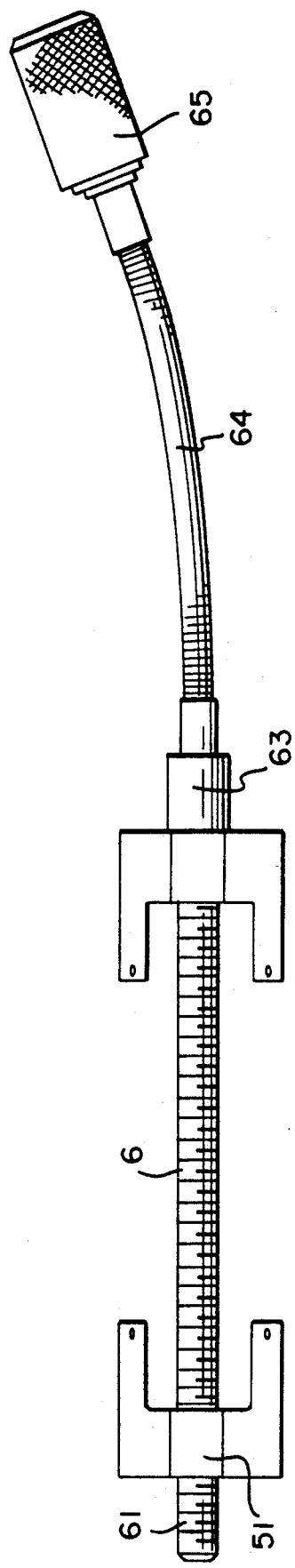
FIG. 5 is a top view of another embodiment of the apparatus of the invention.
Figure 6:
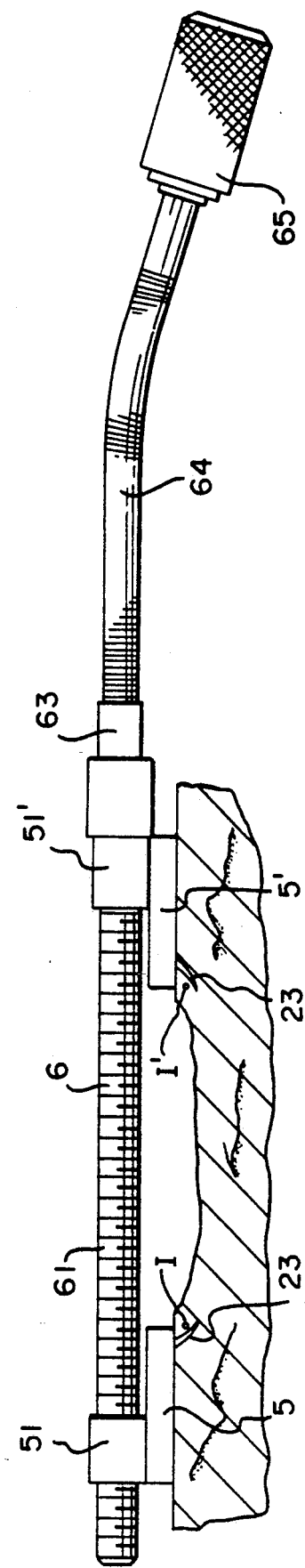
FIG. 6 is a side view of the apparatus illustrated in FIG. 5.

A second embodiment of the apparatus is illustrated in FIGS. 5 and 6, wherein two retaining members 5 and 5' are contracted by a screw 6. The members which are essentially identical with those shown in FIGS. 1 and 2, are provided with perforated lugs 51 and 51' on their respective top surfaces, lug 51 being perforated by a screw-threaded bore and lug 51' by a smooth bore.

The screw 6 includes a screw-threaded end 61 cooperating with the screw thread in lug 51 of member 5, a smooth portion 62 rotating in lug 51', a collar 63 abutting lug 51' and a flexible operating portion 64 terminating in a knob or handle 65. The skin contracting operation is similar to that described with reference to the former embodiment, however it becomes evident that the screw 6 somewhat obstructs the suturing operation.

The illustrated embodiments are shown by way of example. The spirit and scope of the invention is not to be restricted by the preferred embodiment shown.

We claim:

1. A skin closing apparatus comprising:

a plurality of pins configured for insertion underneath skin;

a plurality of U-shaped retaining members; each of said retaining members exhibiting at least two legs in part defining said U-shape and positioned close to the skin when the apparatus is in use, each of said retaining members further exhibiting a sharp skin-piercing hook protruding from a bottom surface of each of said legs; said skin-piercing hooks configured to engage said pins;

a contracting mechanism connecting said retaining members and configured to approximate said retaining members and said pins.

2. The skin closing apparatus according to claim 1, wherein each of said U-shaped retaining members exhibits a flange connected to said legs and defining a bore in parallel alignment with said legs.

3. The skin closing apparatus according to claim 2, wherein one of said U-shaped retaining member bores is a threaded bore, another of said U-shaped retaining member bores is a smooth bore, said contracting mechanism comprising at least a screw extending through said U-shaped retaining member bores.

4. The skin closing apparatus according to claim 1, wherein said plurality of U-shaped retaining members comprises two U-shaped retaining members, each of said retaining members exhibits two legs, a flange connecting said legs and a bore.

5. The skin closing apparatus according to claim 1, wherein said plurality of pins comprises two pins.

6. A skin defect closing apparatus comprising:

a plurality of retaining members, each of said retaining members exhibiting:
   at least two legs,
   a flange connecting said legs and exhibiting a bore located between said legs,
   a plurality of skin piercing elements, each of said skin piercing elements protruding from a surface of one of said legs; and a contracting mechanism connecting said retaining members and engaging one of said flange bores, said contracting mechanism configured to approximate said retaining members.

7. The skin defect closing apparatus according to claim 6, wherein each of said retaining members is configured so said retaining member legs are in parallel alignment.

8. The skin defect closing apparatus according to claim 6, further comprising two pins, each of said pins is configured for insertion underneath skin proximal to a margin of a skin defect, each of said retaining member skin piercing elements engaging one of said pins.

9. The skin defect closing apparatus according to claim 6, wherein said plurality of retaining members comprises two retaining members.

10. The skin defect closing apparatus according to claim 6, wherein each of said skin piercing elements is a skin-piercing hook, said plurality of skin-piercing hooks comprising two skin-piercing hooks.

11. A skin defect closing apparatus according to claim 6, wherein said contracting mechanism comprises at least a screw.

12. A skin defect closing apparatus according to claim 11, wherein one of said retaining member flange bores is a screw-threaded bore, said screw engaging said screw-threaded bore.

13. A skin defect closing apparatus according to claim 11, wherein one of said retaining member flange bores is a smooth bore, said screw exhibits a collar configured to contact said retaining member exhibiting said smooth bore, said screw extending through said smooth bore.

14. A skin defect closing apparatus according to claim 11, further comprising a knob and a flexible portion attached to said screw and said knob, said screw is adapted to be rotated by said knob.

* * * * *

UNITED STATES PATENT AND TRADEMARK OFFICE
CERTIFICATE OF CORRECTION

PATENT NO. : 5,263,971

DATED : November 23, 1993

INVENTOR(S) : Hirshowitz, et al

It is certified that error appears in the above-indentified patent and that said Letters Patent is hereby corrected as shown below:

Column 4, line 12, claim 1, delete "configured to approximate" and insert --approximating--.

Column 4, line 13, claim 1, after "pins" insert --, when said apparatus is in use--.

Column 4, line 16, claim 2, delete "defining" and insert --having at least--.

Column 4, line 27, claim 4, delete "exhibits" and insert --having at least--.

Column 4, line 35, claim 6, delete "exhibiting" and insert -- having at least--.

Column 4, line 36, claim 6, delete "located between said legs".

Column 4, line 40, claim 6, after "mechanism" insert --for--.

UNITED STATES PATENT AND TRADEMARK OFFICE
CERTIFICATE OF CORRECTION

PATENT NO. : 5,263,971
DATED : November 23, 1993
INVENTOR(S) : Hirshowitz, et al It is certified that error appears in the above-indentified patent and that said Letters Patent is hereby corrected as shown below:

Column 4, line 40, claim 6, after "connecting" insert --and approximating--.

Column 4, line 41, claim 6, delete "and engaging" and insert --, wherein said contracting mechanism engages.

Column 4, line 41, claims 6, delete ", said contracting mechanism configured to approximate said retaining members."

Column 6, line 3, claim 4, after "is" insert --rotatable--.

Column 6, line 4, claim 4, delete "adapted to be rotated".

Signed and Sealed this

Twenty-first Day of October 1997

Attest:

BRUCE LEHMAN

Attesting Officer

Commissioner of Patents and Trademarks